(12) United States Patent
Akkerman et al.

(10) Patent No.: US 7,982,868 B2
(45) Date of Patent: Jul. 19, 2011

(54) APPARATUS AND METHOD FOR CHECKING OF CONTAINERS

(75) Inventors: Jensen Peter Akkerman, Huisen (NL); Dan Van Der Meer, Delft (NL); Jilles De Wit, Delft (NL); Sjoerd Van Der Zwaan, Eemnes (NL); Frederik Nico Endtz, Rotterdam (NL); Arend Van De Stadt, Huizen (NL)

(73) Assignee: Eagle Vision Systems B.V., Naarden (NL)

( * ) Notice: Subject to any disclaimer, the term of this patent is extended or adjusted under 35 U.S.C. 154(b) by 770 days.

(21) Appl. No.: 11/658,550

(22) PCT Filed: Aug. 1, 2005

(86) PCT No.: PCT/NL2005/000565
§ 371 (c)(1),
(2), (4) Date: Feb. 7, 2008

(87) PCT Pub. No.: WO2006/011803
PCT Pub. Date: Feb. 2, 2006

(65) Prior Publication Data
US 2008/0291438 A1    Nov. 27, 2008

(30) Foreign Application Priority Data
Jul. 30, 2004   (NL) ..................... 1026747

(51) Int. Cl.
*G01N 21/00* (2006.01)
*G06K 9/00* (2006.01)
(52) U.S. Cl. .................... 356/240.1; 382/142
(58) Field of Classification Search .......... None
See application file for complete search history.

(56) References Cited

U.S. PATENT DOCUMENTS

| 6,498,645 | B1 * | 12/2002 | Knapp et al. | 356/427 |
| 7,342,655 | B2 * | 3/2008 | Yagita | 356/239.5 |
| 2003/0201384 | A1 * | 10/2003 | Yagita | 250/223 B |
| 2006/0208172 | A1 * | 9/2006 | Akkerman et al. | 250/223 B |
| 2009/0279082 | A1 * | 11/2009 | Till et al. | 356/240.1 |
| 2010/0220919 | A1 * | 9/2010 | Leclerc et al. | 382/142 |

FOREIGN PATENT DOCUMENTS

| DE | 19832615 A1 | 2/2000 |
| EP | 0871028 A1 | 10/1998 |
| EP | 1176416 A1 | 1/2002 |
| EP | 1241467 A2 | 9/2002 |

(Continued)

Primary Examiner — Tarifur Chowdhury
Assistant Examiner — Gordon J Stock, Jr.
(74) Attorney, Agent, or Firm — The Webb Law Firm

(57) ABSTRACT

A method for detecting one or more foreign substances in one or more containers filled with liquid, comprising of: transporting the containers filled with liquid in a substantially straight line at relatively high speed in a production environment; —illuminating each container with content with one or more fixedly disposed light sources; and —inspecting the container with content from preferably two or more different orientations using two or more cameras, wherein cameras and lighting are disposed substantially fixedly relative to each other, while the cameras and light sources are mutually connected such that in a short time two or more images of a container filled with liquid can be recorded with mutually differing illumination and/or angle of incidence; —comparing the foreign substances in the two or more images; and —wherein a container filled with liquid is rejected on the basis of the probability distribution obtained from the comparisons, wherein above a determined probability it is concluded that the foreign substance is a glass particle or other undesirable particle.

16 Claims, 15 Drawing Sheets

FOREIGN PATENT DOCUMENTS

| | | |
|---|---|---|
| FR | 2726651 | 5/1996 |
| JP | 9325122 | 12/1997 |
| JP | 11125604 | 5/1999 |
| JP | 2001116700 A | 4/2001 |
| JP | 2002338564 A | 11/2002 |
| JP | 2003306704 A | 10/2003 |
| JP | 2004065775 A | 3/2004 |
| JP | 2004270951 A | 9/2004 |
| WO | 9704887 | 2/1997 |
| WO | 0201207 A1 | 1/2002 |

* cited by examiner

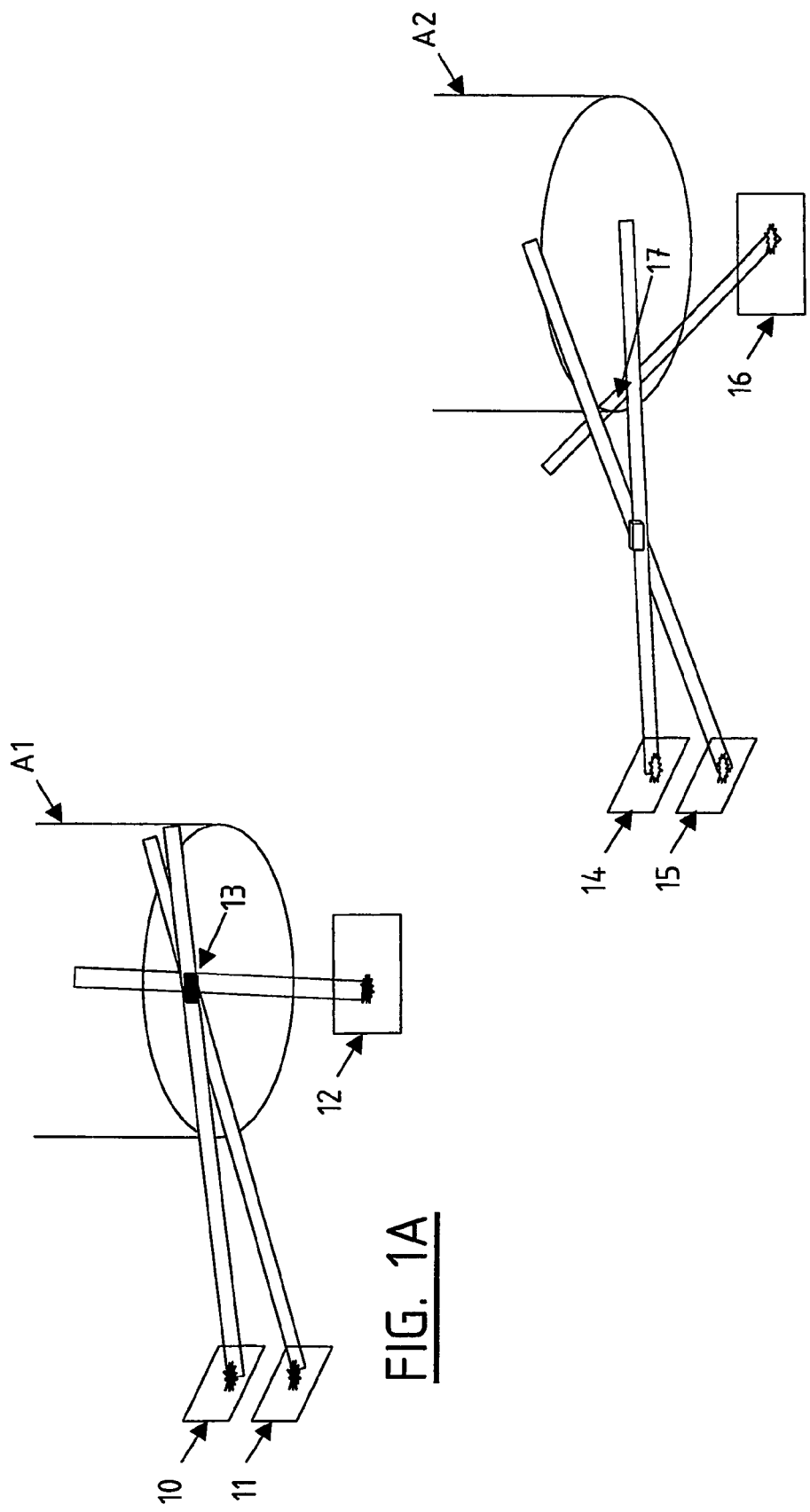

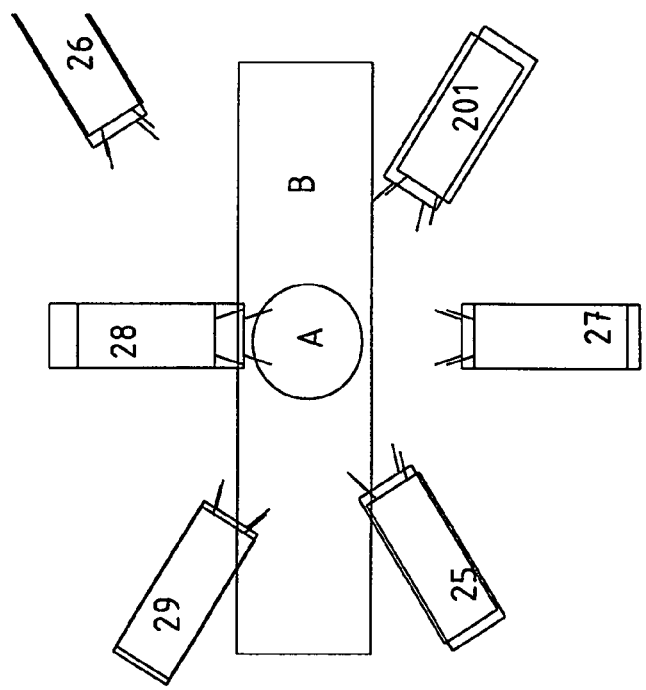
FIG. 2C
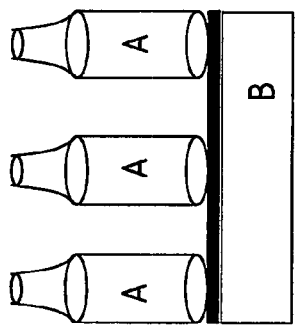
FIG. 2A
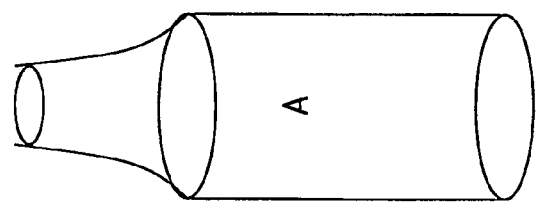
FIG. 2B
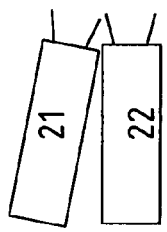

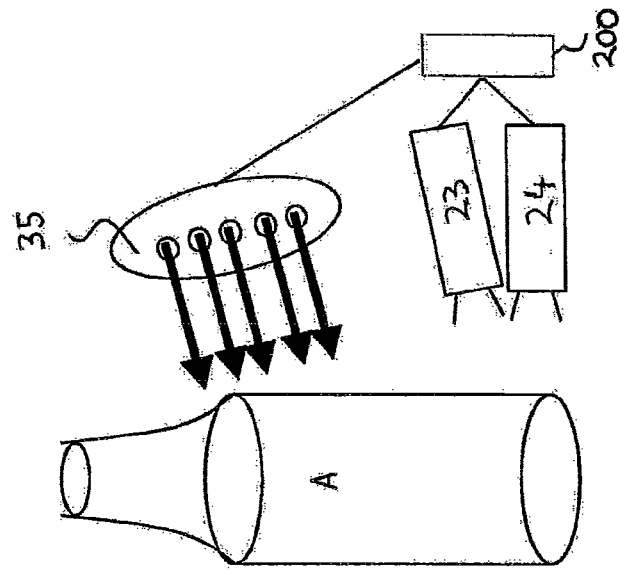
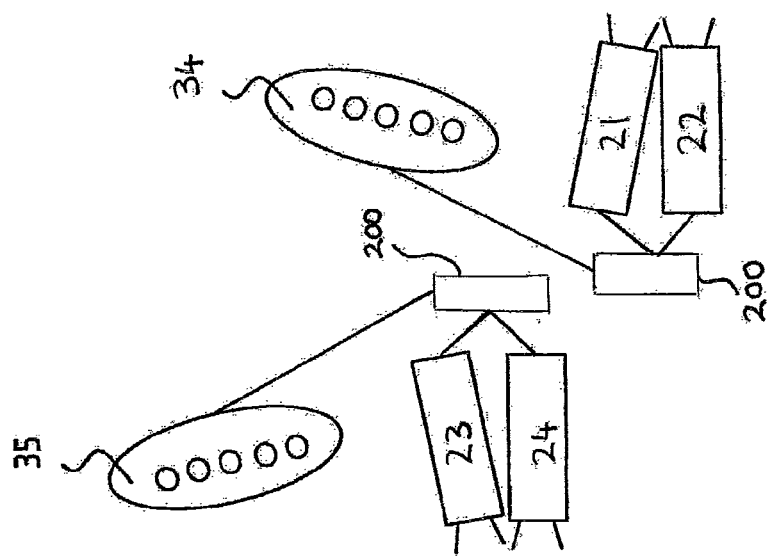
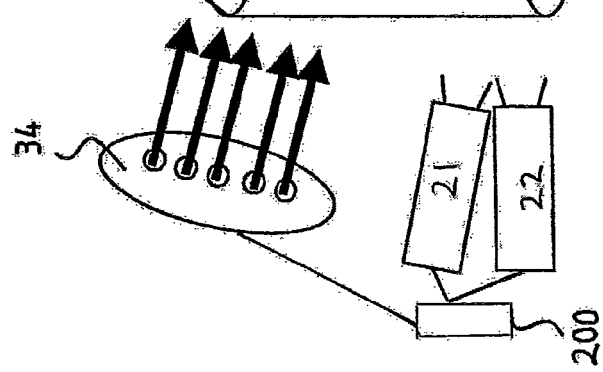
FIG. 3B
FIG. 3A

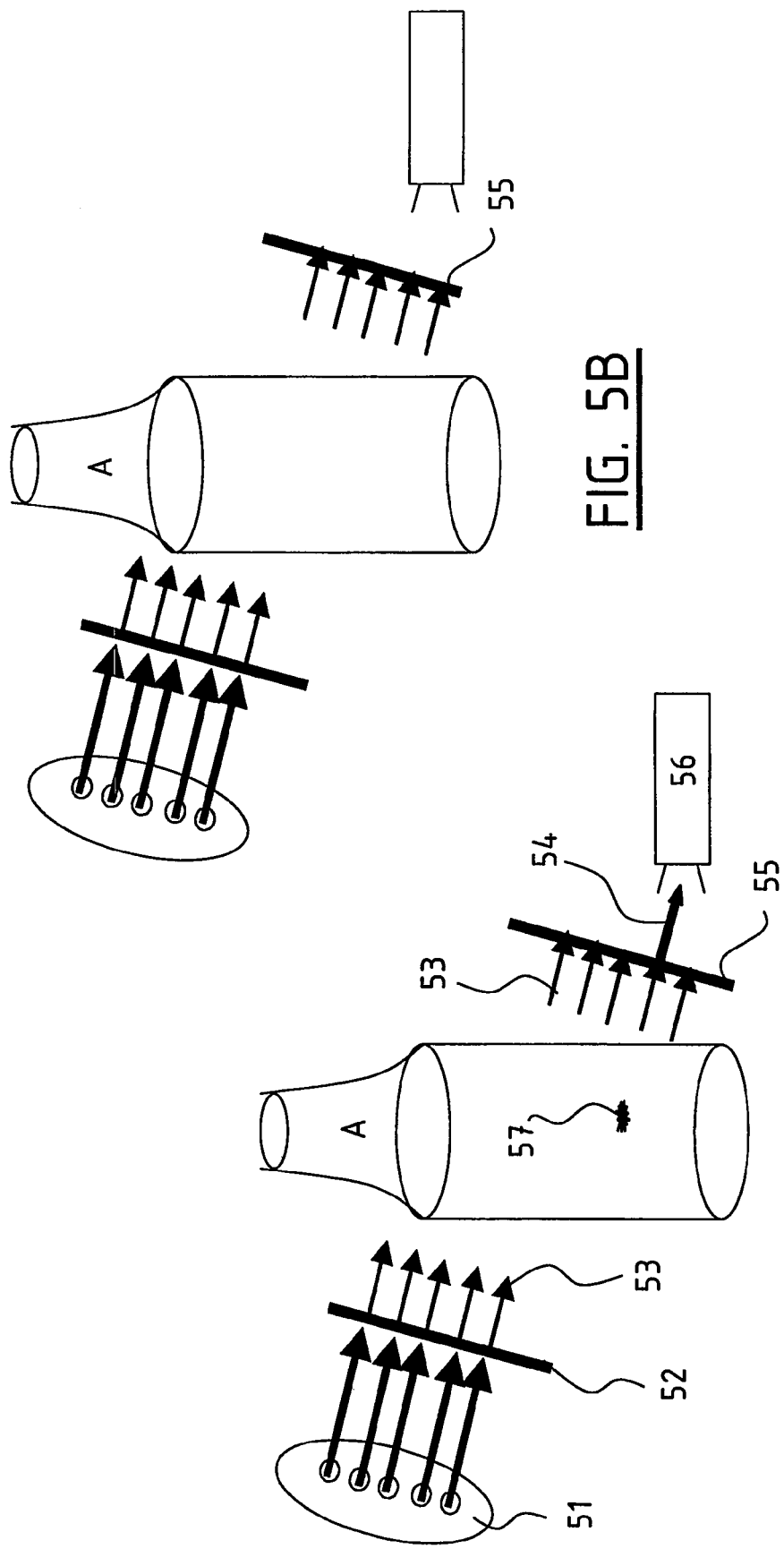

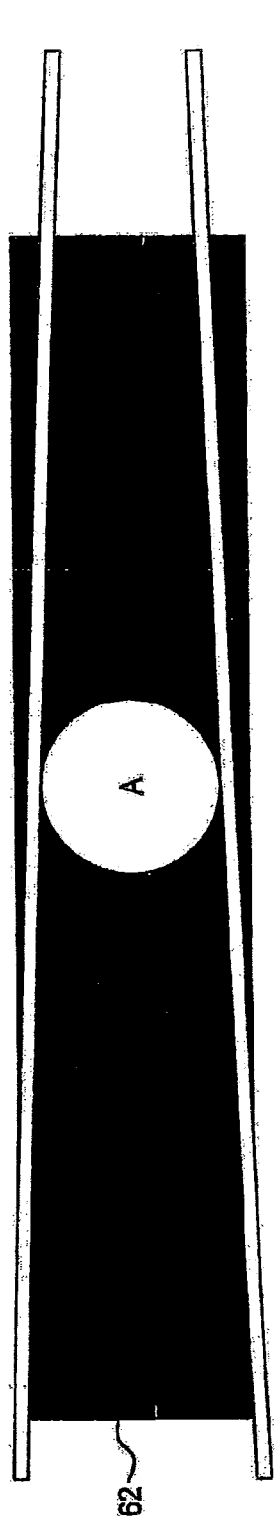
FIG. 6A
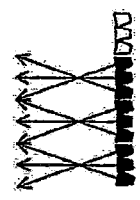
FIG. 6B

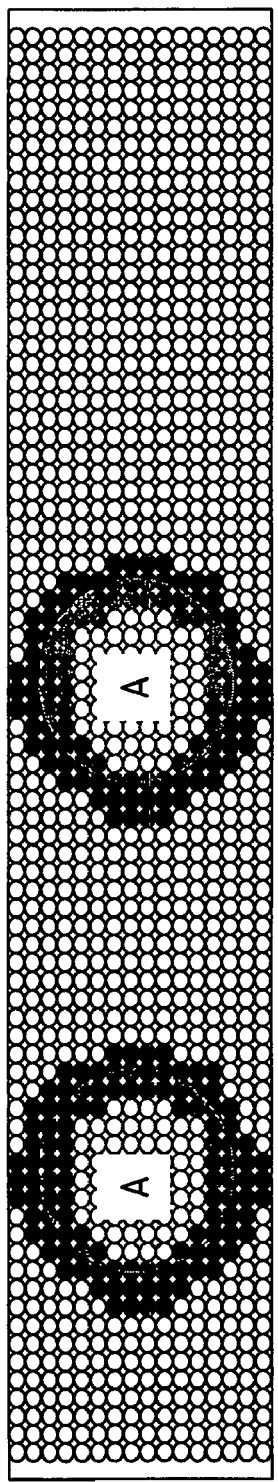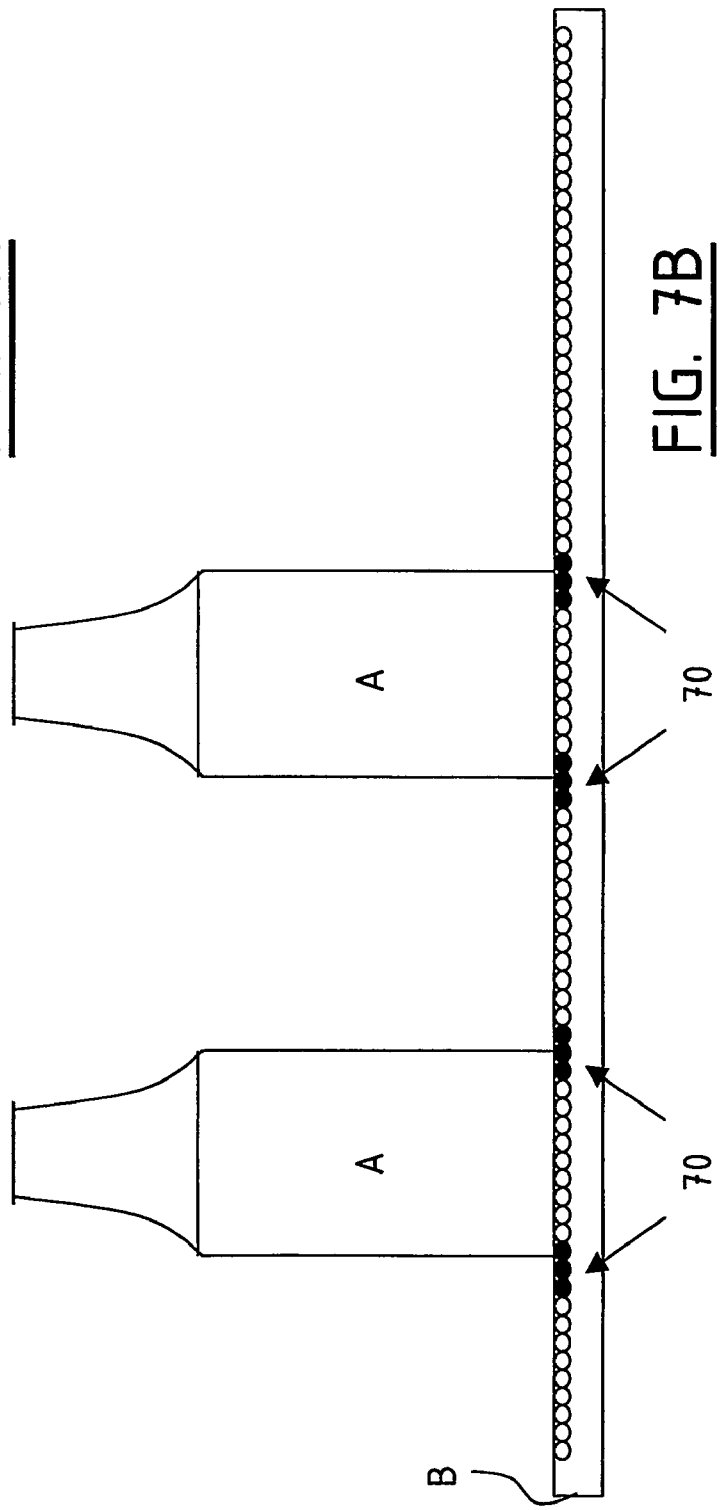
FIG. 7A
FIG. 7B

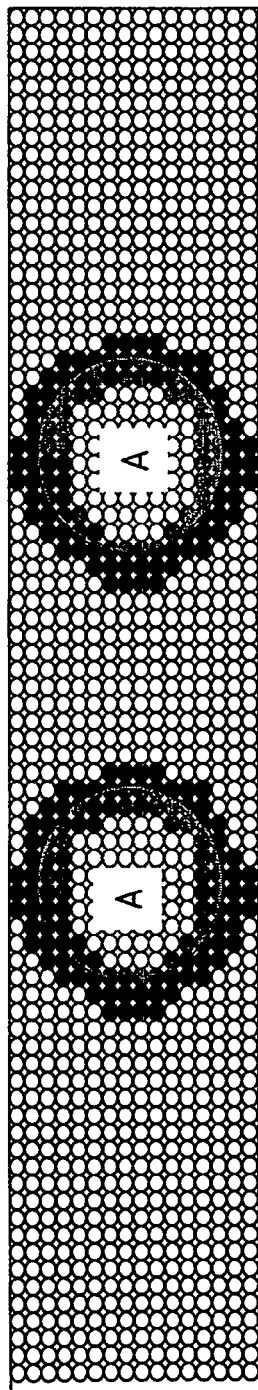
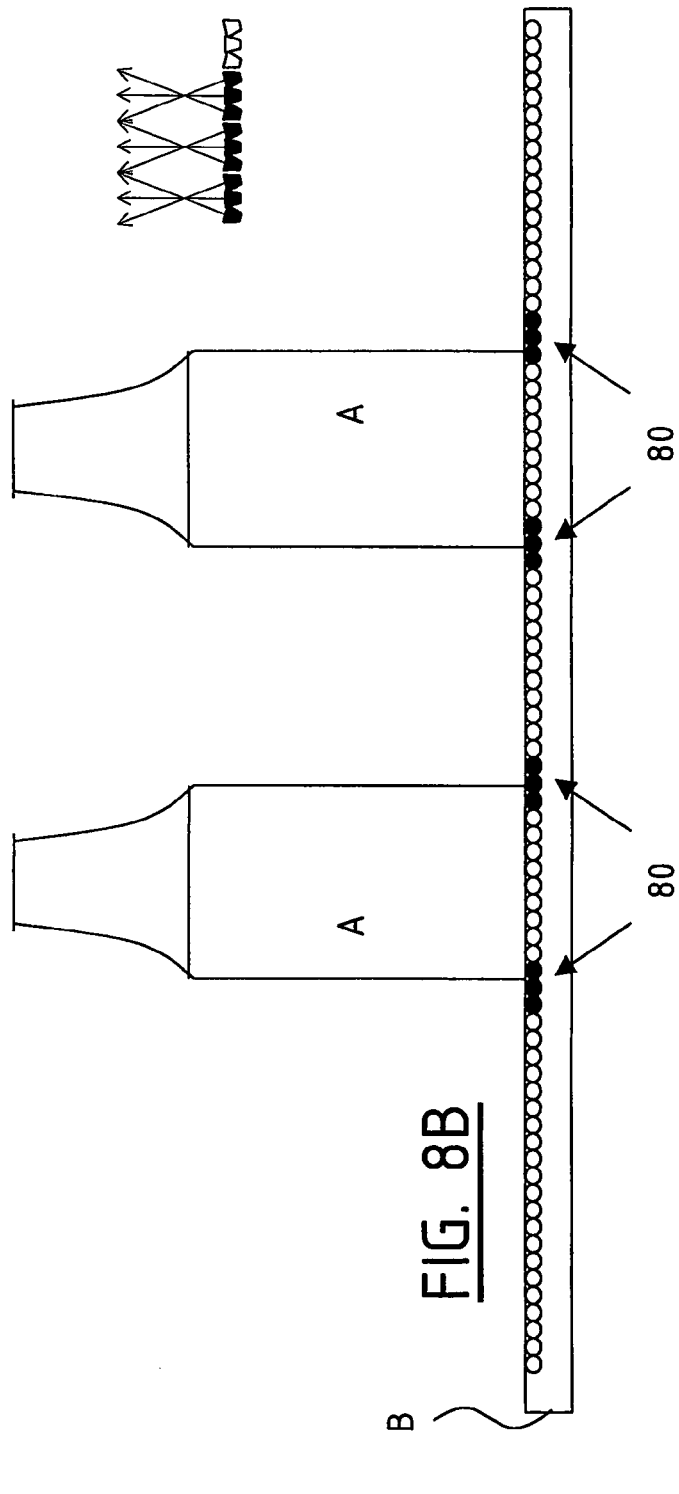
FIG. 8A
FIG. 8B

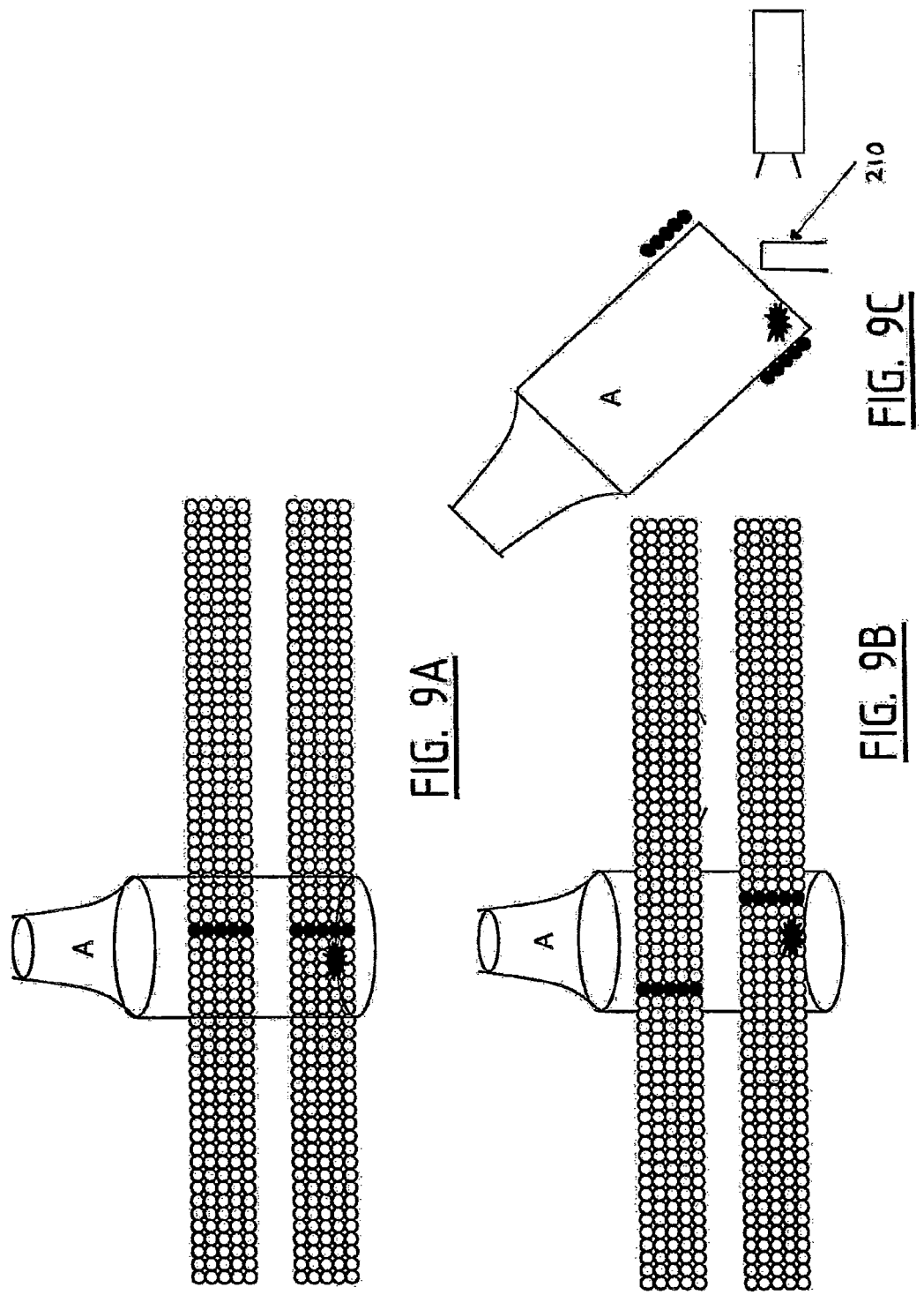

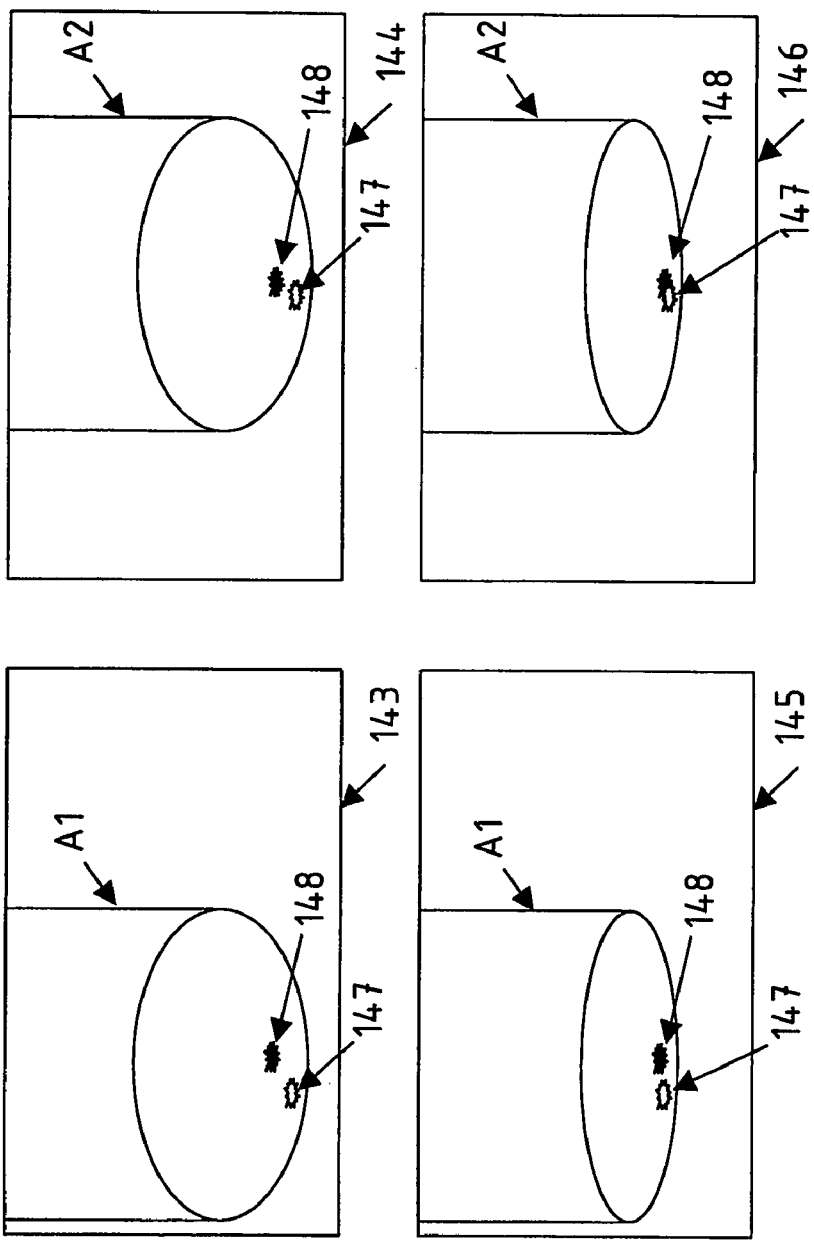
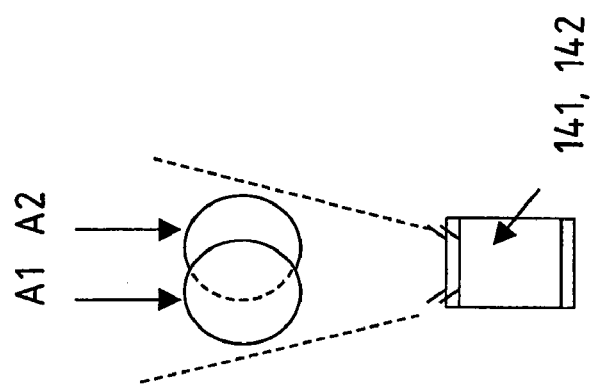
FIG. 13

APPARATUS AND METHOD FOR CHECKING OF CONTAINERS

BACKGROUND OF THE INVENTION

Contamination such as glass in filled containers (with drink such as beer intended for consumption), such as bottles, can be hazardous in the case of human consumption, and in the case of a claim will in any case damage the brand reputation of a supplier.

In a known in-line machine bottles are measured at a number of locations, wherein the bottle is rotated 90° on its vertical axis using a mechanism to enable different views to be realized. This makes the machine relatively large and mechanically complicated. The different inspection units (=cameras) only co-act at the logical level in the decision as to whether or not the bottle must be rejected. If one inspection unit detects contamination, the bottle is rejected. If no inspection unit detects contamination, the bottle is not rejected. This has the drawback that each inspection unit separately must be set with its own rejection threshold. Furthermore, in order to prevent dubious cases and false reject, each inspection unit cannot be given a very sensitive setting. This known machine is hereby not very sensitive and small contaminants cannot be detected (false accept). If however the system is set to be sensitive, a very great deal of false reject then occurs. Glass particles smaller than about 3 mm are generally not visible.

In other machines bottles are irradiated with high-energy (X-)radiation. This can in fact have harmful consequences, and has in any case the association of undesirable influencing of the product for inspecting. In addition, the cost of an X-ray source and detector are relatively high. The basic system will hereby be expensive. In addition, there is a physical limit to the measure of detection because X-ray is based solely on measuring a difference in absorption of rays. Glass particles smaller than about 3 mm are generally not visible.

In other known methods the bottle is actively rotated. The possibility of detecting smaller particles hereby increases, but the embodiment as carrousel requires a complex mechanical set-up which is therefore inherently expensive. A typical number of heads in a carrousel machine is for instance 30 to even 45+24 heads in a 2 star wheel configuration.

SUMMARY OF THE INVENTION

The present invention provides a method for detecting one or more foreign substances in one or more containers filled with liquid, comprising of:
  transporting the containers filled with liquid in a substantially straight line at relatively high speed in a production environment;
  illuminating each container with content with one or more fixedly disposed light sources; and
  inspecting the container with content from different orientations using one or more cameras,
wherein camera(s) and lighting are disposed substantially fixedly relative to each other, while the camera(s) and light sources are mutually switched such that in a short time two or more images of a container filled with liquid can be recorded with mutually differing illumination and/or angle of incidence;
  comparing the foreign substances in the two or more images; and
  wherein a container filled with liquid is rejected on the basis of the probability distribution obtained from the comparisons, wherein above a determined probability it is concluded that the foreign substance is a glass particle or other undesirable particle.

The present invention avoids mechanical handling of a bottle as far as possible. A bottle remains on the conveyor belt in so-called In-line system, capacity 60,000 bottles/hour and higher.

More (>60) images are preferably recorded of one bottle. These images are recorded and processed in rapid succession with different cameras, different angles of view, different lighting directions, different lighting methods/wavelengths and at different bottle positions. The images are combined and processed in integrated manner so as to arrive at an end result for the bottle.

Use is made in processing of a 3D geometric model of the bottle and particle in order to determine whether a possible particle or reflection is inside the bottle or on the inner or outer side of the bottle wall.

Combining two (or more) images of the same object to a 3D position by so-called stereovision according to the present invention is applied in order to determine whether an undesirable object (contamination or for instance reflection on the wall) is inside a bottle or not.

Combining information from light of different wavelengths (multi-sensor fusion) is applied according to the present invention in order to determine whether an object is undesirable (for instance glass) or not.

Variations in images are obtained, among other ways, by:
1) different cameras at different positions/orientations
2) different lighting direction
3) different lighting method/wavelength.

The light source is preferably switched such that both dark field and light field images can be obtained.

The present invention further provides a device wherein the method can be applied.

BRIEF DESCRIPTION OF THE DRAWINGS

Further advantages, features and details will be elucidated on the basis of the following description of preferred embodiments thereof with reference to the accompanying drawing, in which:

FIGS. 1A and 1B show respectively schematic image recordings of a bottle with a foreign substance;

FIGS. 2A, 2B and 2C show respectively a side view, a side view and a top view of a first embodiment of a device for performing the method according to the present invention;

FIGS. 3A and 3B show respective side views of a preferred embodiment of a method according to the present invention in respectively a first and second position;

FIGS. 5A and 5B show respective preferred embodiments of a method and device according to the present invention;

FIGS. 6A and 6B show respectively a top view and side view of a further preferred embodiment of the present invention;

FIGS. 7A and 7B show respectively a top view and side view of a further preferred embodiment of the device of the present invention;

FIGS. 8A and 8B show respectively a further preferred embodiment of a method and device according to the present invention;

FIGS. 9A-9C show respective side views of a preferred embodiment in a first switched position and in a second switched position;

FIG. 13 shows schematic illustrations of the match process in the case of a moving bottle;

DETAILED DESCRIPTION OF THE INVENTION

Figure 4:
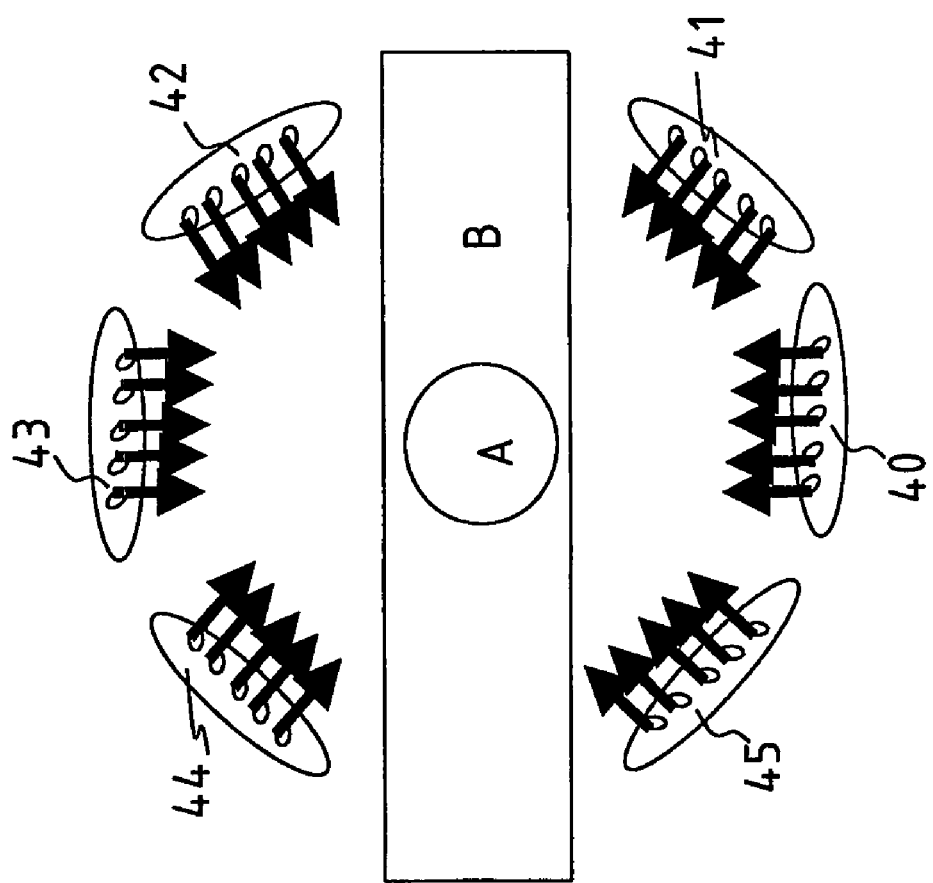
FIG. 4 is a top view of a preferred embodiment of the invention.

FIG. 1 shows bottle A1 and bottle A2 with possible flaws 13 and 17 therein. The possible flaw 13 is a real flaw, possible flaw 17 is an embossing on the outside of the bottle, and so not a real flaw.

Camera images 10, 11, 12, 14, 15 and 16 are images recorded from different cameras and/or at different times and/or different positions. In this example 10, 11, 14 and 15 are via the side of the bottle and 12 and 16 via the bottom. Other combinations are also possible.

By combining information from these different images the three-dimensional (3D) position of the possible flaw can be reconstructed with so-called stereovision techniques.

Using 3D information of the possible flaw combined with the dimensions of the bottle it is possible to determine whether the particle is located inside or outside the bottle.

For optimum detection reliability it is necessary to use as many points of view as possible. In FIG. 2 bottle A on conveyor B is inspected from twelve directions by making use of six camera pairs. Cameras 21 and 22 form a pair, and cameras 23 and 24 also form a pair. These pairs, 25-201, can be placed around bottle A and conveyor B.

For optimum detection reliability as many lighting sources as possible can be used. In FIGS. 3A and 3B two sources 34 and 35 are placed opposite each other relative to bottle A. All light sources can be on simultaneously, and it is also possible to switch light sources on and off in time and to record images from different viewpoints. A control unit 200 controls the operation of light sources 34, 35 and cameras 21, 22, 23 and 24.

In FIG. 4 bottle A on conveyor B can be illuminated from a plurality of positions. Possible positions are 40 to 45.

In FIG. 5 unpolarized light from a light source 51 is polarized by a linear polarizer 52. The linear polarized light 53 passes through bottle A and is incident upon a second linear polarizer 55 which is rotated 90 degrees in polarization. A glass particle 57 can give a different polarization direction to the light so that light 54 still arrives in the camera 56 through the second polarizer 55. If there is no glass particle present in bottle A, the polarization direction of the light does not change appreciably, and little or no light will therefore pass through polarizer 55.

The lighting can also be embodied as in FIG. 6. A bottle A is advanced over a flat uniform lighting 62 which consists of for instance LEDs. Two belts provide for the forward movement of bottle A over this plate.

The lighting can also be embodied as in FIG. 7. A bottle A is advanced over a flat plate 71 consisting of a large number of LEDs. Bottle A is advanced over the plate. Individual LEDs 70 are switched on only at the position where bottle A is situated.

The lighting can likewise be embodied as in FIG. 8. A bottle A is advanced over a flat plate 81 consisting of a large number of LEDs. The bottle is advanced over the plate. Individual LEDs 80 are switched on only at the position where bottle A is situated. The difference with FIG. 7 is that the bottles have been moved further along.

In the exemplary embodiment of FIG. 9 the bottle is tilted slightly, for instance in a manner not shown using a mechanically accurate worm wheel, so that it is possible with a camera to inspect, through the bottom of the bottle, the area of the bottle where the foreign substance should be situated. In this embodiment the LED lighting is directed at the side wall of the bottle.

As shown in FIGS. 9A and 9B, the lighting on either side of the bottle can be switched such that it changes and the bottle as it were (virtually) moves in that the lighting moves relative to the bottle. A number of images are then recorded each time in short succession with the camera. An actuator 210 is shown in FIG. 9C for placing each container in oblique position.

Figure 10:
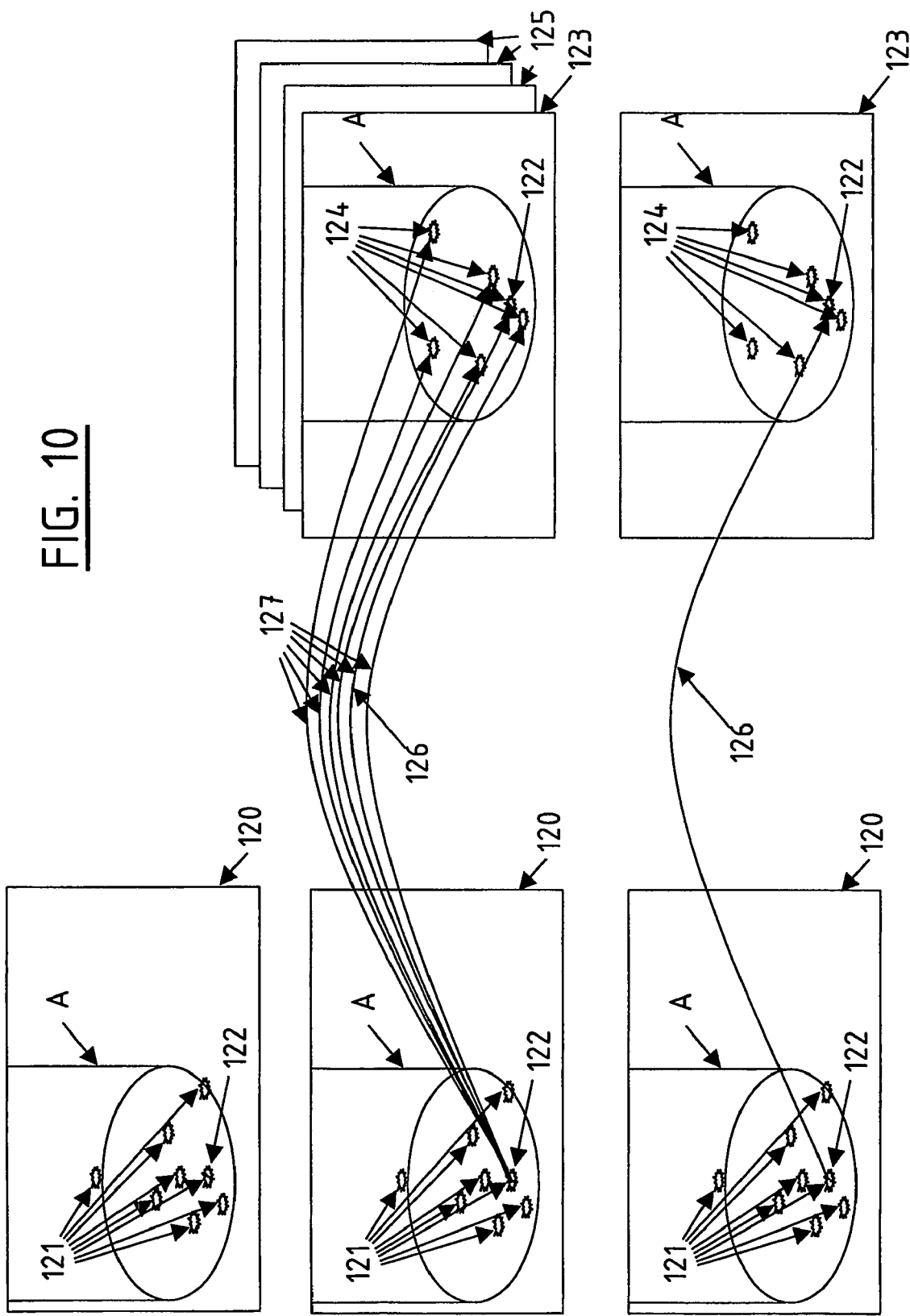
FIG. 10 shows schematic illustrations of the so-called match process according to the present invention.

Images are recorded and stored on the basis of a single of the described optical methods or a combination thereof. The further processing of the images is shown in FIG. 10.

An image 120 is made of bottle A. A number of possible flaws 121 are detected by means of known image processing techniques as described above. Of these possible flaws 121 in the figure, flaw 122 is the real flaw for detecting. Each possible flaw 121 has a number of computed features (such as form, colour, size, position and other features). During the detection of possible flaws the system sensitivity is set such that the real flaw is almost certainly detected as possible flaw. The consequence hereof is that the number of possible flaws that are not a real flaw is probably relatively high. In order to reduce false reject because of these possible flaws that are not real flaws, a follow-on operation is provided wherein the number of possible flaws is decreased without eliminating the real flaw.

Another image 123 of bottle A is recorded and processed at another moment and/or position (by means of the described image processing techniques). The possible flaws 124 are detected from image 123. Of these possible flaws 123 in the figure, flaw 122 is the real flaw for detecting. Features of these possible flaws are also computed (such as form, Colour, size, position and other features).

The computed features of possible flaws 121 and 124 are combined as follows. Of each possible flaw 121 a combination 127 is made with a possible flaw 124. Of this combination the likelihood is computed of both possible flaws being (parts of) a real flaw. For instance by measuring the similarity in form: the greater the similarity between 121 and 124 and a real flaw, the greater the likelihood that they are both the same real flaw. Other methods of determining probability are also possible.

Combinations 127 are created in the case of possible flaws 121 in image 120 and possible flaws 121 and 124 in image 123. Among these is situated the combination 126 of the real flaw. Combination 126 can be found by applying an appropriate selection, such as selection of the most probable. It is also possible to compute features derived from a combination which are derived from the specific combination of the two possible flaws. An example is the three-dimensional position of a possible flaw in the bottle. This can be derived from the positions of the possible flaws in the individual images 120 and 123 by stereovision techniques that are assumed known. A three-dimensional position of a combination in the vicinity of a position where real flaws often occur (for instance in the inside edge on the bottom) increases the likelihood of this combination.

Each combination of the possible combinations is then combined with all possible flaws of other images 125. These images are recorded at another moment and/or position of the same bottle A. These combinations of combinations result in a large number of possible combinations, among which the combination 126 of the real flaw 122 is to be found.

The most probable combination(s) (for instance the 10% of possible flaws with the highest probability) is/are selected by a selection process. Finally, on the basis of the features and derived features of the possible flaws associated with this/these combination(s), it is determined whether at least one real flaw is detected. If this is the case, bottle A is then rejected.

Figure 11:
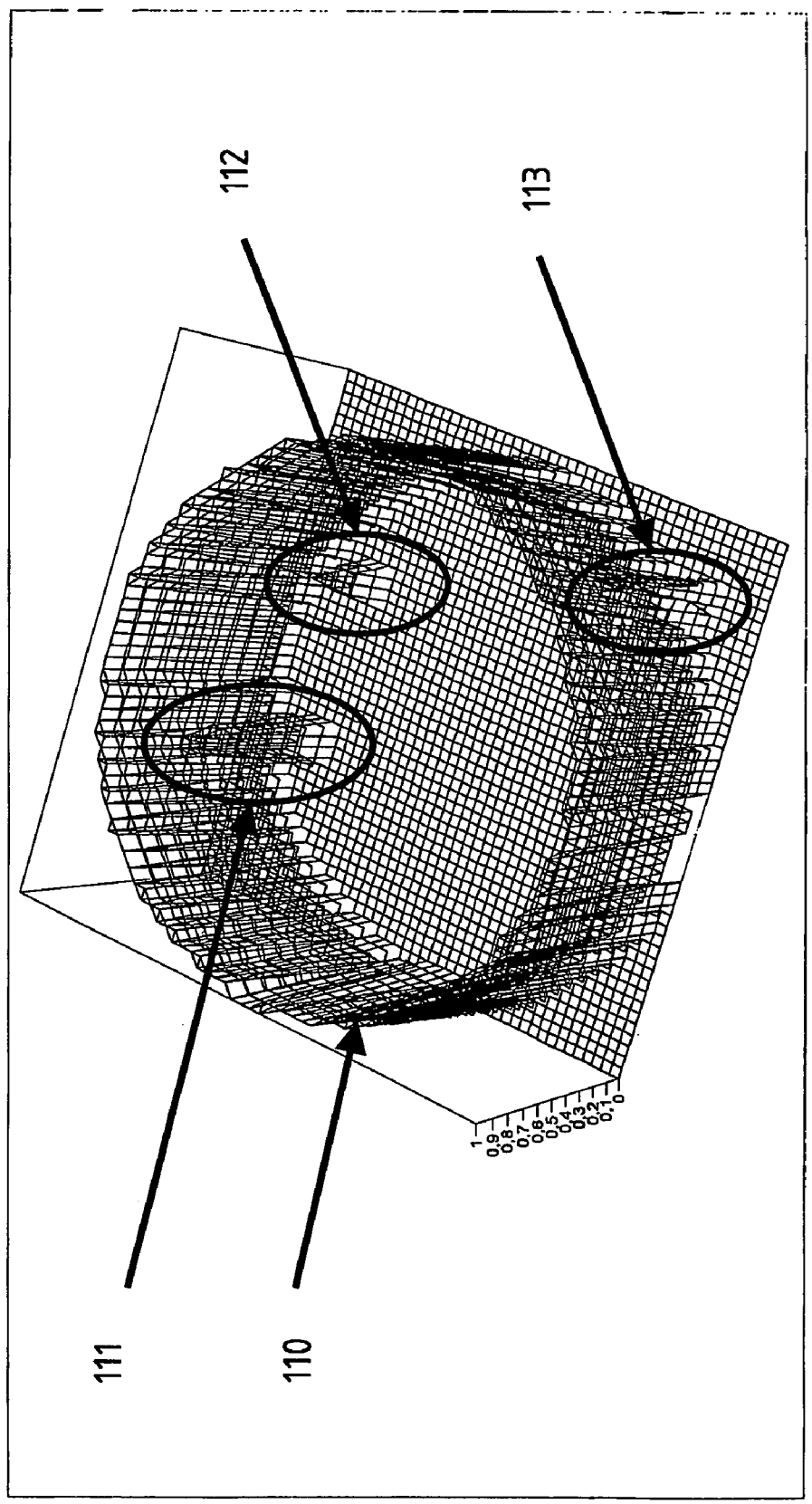
FIG. 11 is a graphic representation of a possible probability distribution obtained with the match process of FIG. 10.

FIG. 11 indicates the likelihood of a determined part of the bottom of the container being an undesirable (glass) flaw. The edge of the bottle is indicated at 110, wherein there is a high probability of it being glass. By analysing the form of this area of continuous high probability it is concluded that this is the (normal) edge of the bottle.

The position of an undesirable glass flaw is indicated at 111. There is a high probability of (undesirable) glass locally.

A position of a perhaps undesirable glass flaw is indicated at 112. There is a low probability of (undesirable) glass locally. This can be a small particle or an irregularity on the bottom.

A position of an (undesirable) glass on the outside of the bottle can be seen at 113. This is for instance an embossing or the bottle wall.

Bottle A1 and A2 in FIG. 13 are the same bottle A shown in succession (and meanwhile transported). Cameras 141 and 142 are placed one above the other and the image field of each is such that bottle positions A1 and A2 are in view. Images 143 and 144 are recorded in succession by camera 141, the camera which is placed above camera 142 and inspects the bottom of the bottle more from above than camera 142. Images 145 and 146 are taken by camera 142.

Two possible flaws 147 and 148 are indicated in all four images: 147 is a possible flaw on the outside of bottle A (for instance a so-called embossing). Possible flaw 148 is a real flaw on the bottom on the inside of the bottle at the edge.

By computing the positions of possible flaws in the four images (e.g. with template matching techniques) and computing the differences in these positions, the relative three-dimensional position between possible flaws 147 and 148 can be determined.

Shown as example in FIG. 13 is that in image 143 (recorded at bottle position A1) possible flaw 147 is situated at a distance to the left of possible flaw 148. In image 144 (recorded at bottle position A2) this distance has been significantly reduced. This means that possible flaw 147 is situated closer to the camera than possible flaw 148. It is thus possible to compute the distance of possible flaw 147 and 148 from the camera.

An exemplary setup (FIG. 2) consists of six camera pairs. The two cameras of a pair are for instance located one directly above the other, wherein they inspect the same point in the bottle at a small mutual angle. Each pair records an image simultaneously and can thus be used as a stereo pair. This means that in theory the 3D position (relative to the camera position) of a point that is visible in both cameras can be computed. There are six of these pairs, whereby recordings of a bottle are made from six directions.

The illumination is varied by recording an image with front illumination and/or then an image with back illumination (and/or possible variations such as from the side). An image can also be recorded with multiple illuminations on simultaneously if detection is then found to work better. The lighting intensity can also be varied so that images of the same bottle at different levels of illumination are used.

The illuminators can be embodied with the same or different wavelength(s) or light intensities.

Specific lighting effects, such as the use of polarized light, can also be applied.

In order to further increase the chance of detection, a plurality of images are made of each bottle. Because the bottle moves (slightly), the view also changes slightly and the particle can become visible.

The overall image processing methodology is:
1) to generate (many) candidate contaminants (=flaws) from the image data
2) to combine flaws from different images into a 3D flaw
3) to remove unlikely or impossible 3D flaws
4) to reject the bottle if a 3D flaw remains.

The chance of false accept is minimal due to the strategy of generating many candidate contaminants and then eliminating the erroneous candidate contaminants by means of software.

It is also possible, to add an activator in line to the system beforehand, which ensures that a possible particle in the bottle moves slightly, thereby increasing the chance of it being visible. This can be for instance a jolting/bumping means which touches the bottle briefly or an ultrasonic signal causing a vibration in the bottle.

The present invention provides several advantages, such as:
  practically no mechanical handling of the bottle is required. There are therefore lower tooling costs for similar systems, resulting in lower costs and/or a greater margin;
  implementation can take place in existing lines without structural modifications to the conveyor belt; carrousels and layout modifications are unnecessary.

As addition to the system, extra functionality can be added to the production line at the same location in order to inspect a finished and filled bottle. Owing to the relatively small dimensions of the in-line FBI there is still sufficient space in most production lines for extra functionality as stated below. An integrated and complete end-of-line inspection of a filled bottle is hereby possible at a small location:
  cap integrity functionality: inspection of the decoration of the cap and of the closure by placing a camera which inspects the bottle from above. Comparison by means of software of the anticipated cap and the real cap;
  rim on the inside: illuminate rim from inside by optical method and inspect it with a camera;
  filling level of the bottle: can be measured by for instance a side view. Filling level of liquid relative to crown cap/cap. There may be differences in 30 absolute filling level of liquid relative to bottle 8 due to variations in bottle dimensions. The consumer is mainly interested in the filling level relative to the cap since differences relative to the cap are most noticeable;
  neck-label position and quality;
  front and back label position and quality (e.g. as described in the TLI patent application);
  product mix-up detection by checking that, of a determined bottle, the cap, bottle, the product itself and the label have the correct colour, structure, form and decoration (product mix-up detection with camera technique).

The recorded images are processed so as to detect candidate contamination flaws. For this purpose the images are processed in per se known 2D manner to obtain flaws (groups of connected pixels) representing possible contamination. The techniques make use of for instance dark field illumination, bright field illumination, edge detection, background subtraction (self-learning), stereo by matching part of image 1 with a part of image 2 (match displacement is then a measure for the distance of the particle from the camera), and other methods.

The outcome is a list of flaws (per image) showing possible contamination. Each flaw is provided with its features, such as for instance position, intensity and size.

The flaws of an image are compared (matched) with the flaws of the other images. This matching can take place by comparing any image with any other image. However, with a number of flaws of 10 per image and 60 images, this then results in 1060 possibilities to be inspected. In practical terms this is a relatively large number for real-time inspection. This is referred to as 2D to 2D matching.

Another method is to match the flaws of each image with a general (3D) image of the bottle. The 60 images are each then inspected 10 times (=600 times). The 3D image of the bottle could for instance consist of the bottom including the height of a (possible) particle lying on the bottom. This is referred to as 2D to 3D matching. An example is given in FIG. 11 of an artificially constructed image of the bottom of the bottle having as Z value the likelihood of there being glass at this position on the bottom. The edge of the bottle is clearly visible as value Z, since a part of the wall will always be visible at some point in the recorded images. Two particles are shown, particle 111 with a great likelihood of being glass, and particle 112 with a lesser likelihood.

At least 2D-2D and 2D-3D matching are possible with the techniques described in this application.

Figure 12:
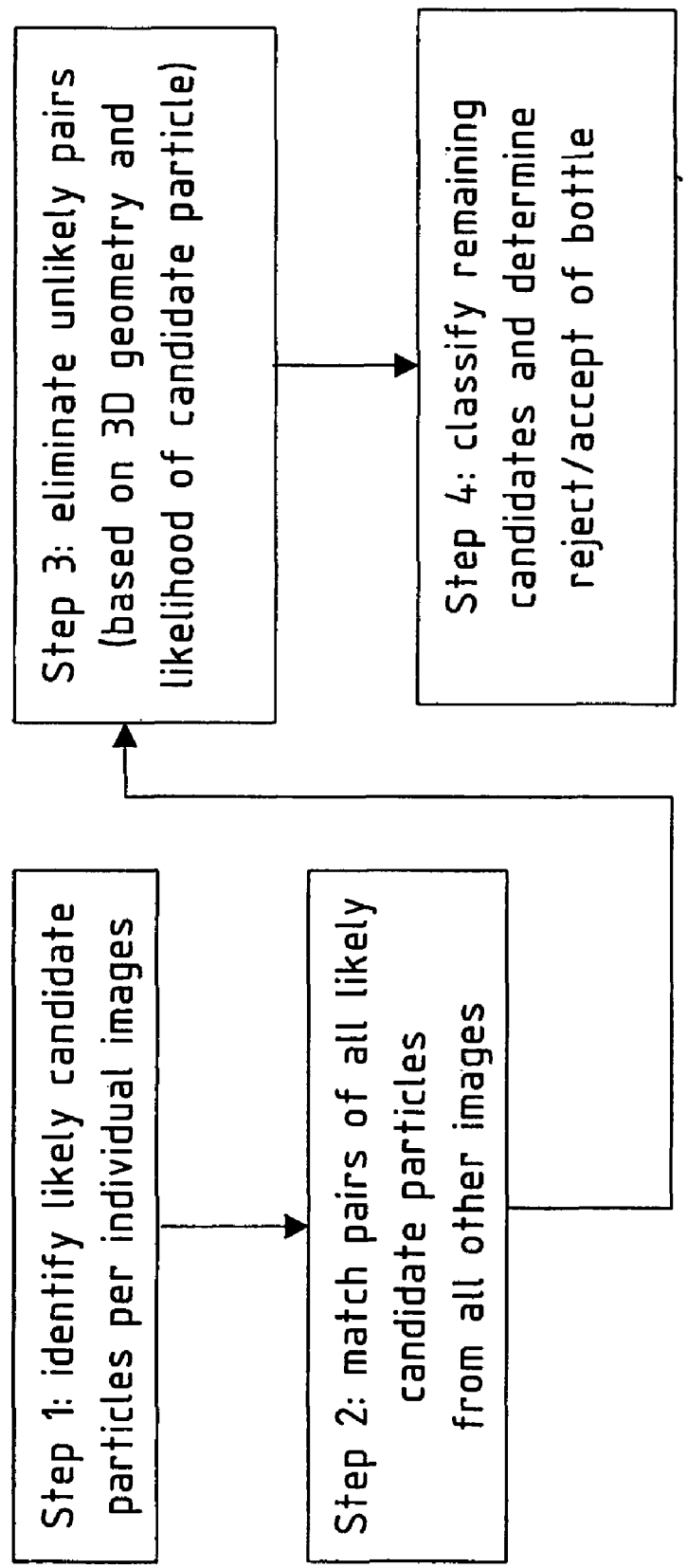
FIG. 12 shows a block diagram of the process for rejecting/accepting a bottle.

As shown in FIG. 12, at step 1, likely candidate particles are identified in each image. At step 2, all likely candidates from step 1 are matched. The outcome of the matching will bring about a relatively large amount of false reject because each possibility is considered. In step 3 the possibilities must be eliminated systematically as stated in FIG. 13. In a preferred embodiment step 2 and 3 can be performed iteratively (a number of times in succession), wherein more and more candidates are removed and with those remaining a determination is once again made as to which give the best overall match.

The final decision as to whether a bottle is rejected is taken at step 4 on the basis of the features of the remaining candidate contaminants.

A preferred embodiment comprises for instance the following hardware:
Flashing LED illuminators 4-12 units.
Timing of image recording and illuminator derived from 1 trigger and encoder information.
Image field of underside of bottle or whole bottle to detect foils and floating objects.
(Firewire) IR camera 80 frames/sec or more. Asynchronous reset camera.
Infrared illuminator with (modified) dark field illumination.
Extra (colour) cameras for label inspection, cap integrity, fill level inspection on fixed world (or carrousel).
Vision computers (IPPs) and communication computer (COMMPC) on fixed world.
System software and architecture (IPPs and (COMMPCs) for camera triggering, switching to IPPs, image storage, network, user interface, processing kernels, inspection and system parameter management.
Application software for flaw detection (subtraction image analysis and average subtraction image correction) and support tools (On-line validation tool, Elimination Test Bottles, Off-line parameter optimization tool, Desk Top Image Analyser, Foam and Bubble Filter).
Hardware embodiment for industrial environment: camera, illuminator, system housing, IPP PC, COMMPC. This means IP65 compliant.

Further embodiments comprise the following aspects.

Figure 14C:
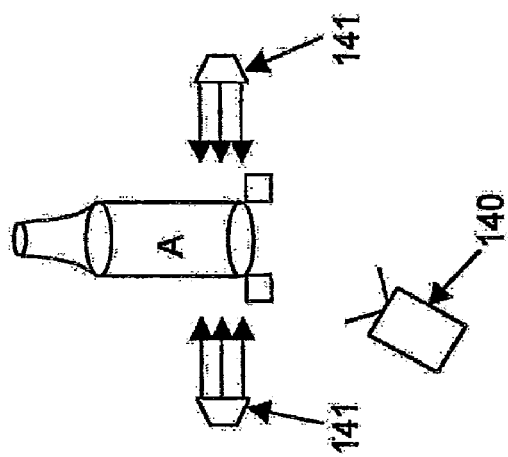
FIGS. 14A-C show schematic illustrations of further preferred embodiments according to the present invention.
Figure 14B:
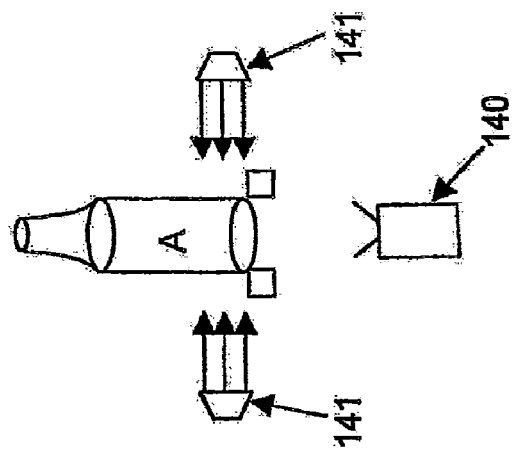
Figure 14A:
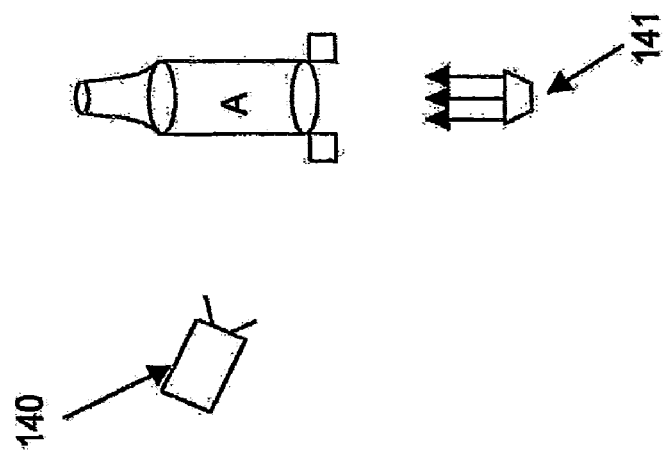

The bottle can be illuminated and inspected according to a number of methods (FIG. 12), for instance
(1) with the lighting 141 on the underside and camera 140 from the side (FIG. 14A)
(2) with the lighting from the side and the camera straight from below (FIG. 14B)
(3) with the lighting from the side and the camera obliquely from below (FIG. 14C).

Figure 15A:
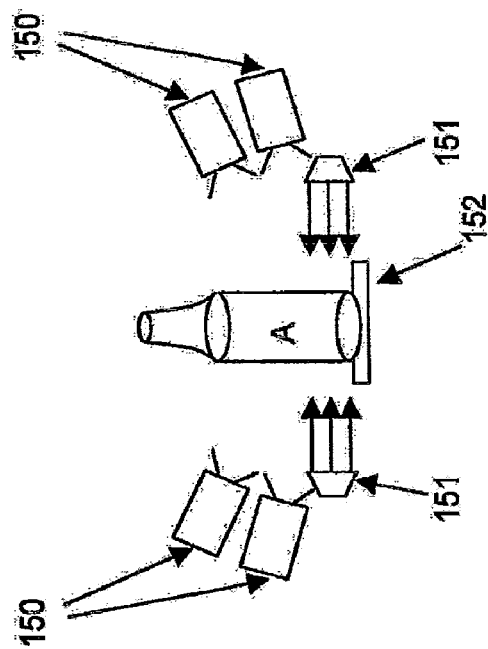
FIGS. 15A-C show schematic illustrations of further preferred embodiments according to the present invention.
Figure 15B:
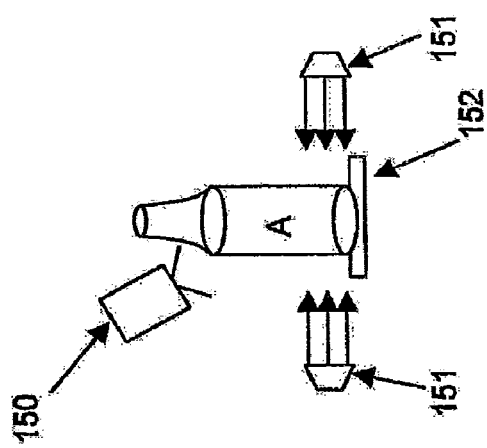
Figure 15C:
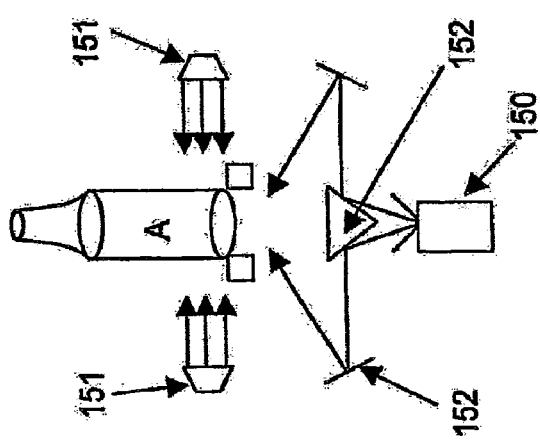

Advantages of method (2) and (3) are that:
The whole bottom is in view in each recording, whereby a glass particle can be seen sooner and in more successive recordings. The inspection time can possibly be shortened hereby. Tracking and classifying particles through different recordings by means of software also becomes simpler.
Optional drying of the bottle can remain limited to the bottom of the bottle because the imaging (and possible deformation by water) takes place there.
An additional advantage of (3) is that it is possible to view for the greater part along the edge of the head glass particles lying in the edge of the bottom. Cleaning of the camera is also relatively simple in (3) because of the position of the camera.
As variant it is also possible using mirrors, prisms 152 or other aids to look into the bottle obliquely from below simultaneously from two or more views using one or more cameras 150. The chance (1) of the particle reflecting light in the direction of the camera hereby increases and the chance (2) of the particle not being visible behind the edge of the head hereby decreases (FIG. 15A).
It is also possible as variant to look into the bottle from above via the so-called shoulder of the bottle (FIG. 15B).
It is also possible as variant to realize two stereo pairs on either side of the bottle using four cameras 150 (FIG. 15C). As a result of illumination with lighting 151 as according to the above described methods, bottle support 152 can be embodied without being transparent for lighting and/or camera. The advantage hereof is that minimal modifications have to be made to the conveyor belt.

The images can be recorded and processed in accordance with a number of methods. The recording of the images can be triggered as a result of the orientation of the bottle by for instance a sensor which gives a signal at a determined bottle orientation, or can be triggered by time, for instance by a sensor which gives a signal at regular or random moments.

The processing of recorded images can take place in at least three ways:
(1) subtracting from each other images with the same orientation of the bottle and analysing the subtraction image for the outcome;
(2) converting a recorded image to a previously recorded image by "back rotation/displacement" of the image to the orientation/position of a previously recorded image, and then further processing as according to method (1).
(3) Tracking particles over multiple images and describing the path of the particle (two or three-dimensionally). Determining on the basis of the parameters of the path whether the particle is glass (reject) or whether it is organic material or the like (accept).

The invention claimed is:

1. A method for detecting one or more foreign substances in one or more containers filled with liquid, comprising the steps of:
   transporting one or more containers filled with liquid;
   illuminating each container with content with one or more fixedly disposed light sources; and
   inspecting each container from two or more different orientations using two or more cameras,
   wherein cameras and lighting are disposed substantially fixedly relative to each other, while the cameras and light sources are mutually switched such that two or more images of each container can be recorded with mutually differing illumination and/or angle of incidence; and
   comparing foreign substances in the two or more images;
   wherein a container is rejected on the basis of a probability distribution obtained from the comparisons, and wherein above a determined probability it is concluded that a foreign substance is a glass particle or other undesirable particle.

2. The method as claimed in claim 1, wherein illumination takes place by means of a number of light sources which are switched such that during transport of each container, images are recorded according to both a dark field technique and a bright field technique.

3. The method as claimed in claim 1, wherein the light sources are switched as the lighting rotates around each container.

4. The method as claimed in claim 1, wherein by using two cameras disposed at different angles, it is determined whether a foreign substance is situated inside or outside each container and/or whether the foreign substance is a glass particle.

5. The method as claimed in claim 1, wherein use is made of polarized light.

6. The method as claimed in claim 1, wherein use is made of infrared light.

7. The method as claimed in claim 1, wherein the containers are transported over a transporting part provided with light-emitting diode (LED) light sources and wherein the LEDs are switched such that the lighting co-displaces with the containers filled with liquid.

8. The method as claimed in claim 1, wherein a plurality of LEDs are arranged laterally of the containers, and each container is tilted on a transporting device so as to enable a camera to be directed at the bottom thereof and to cause a foreign substance to move to the image field of the camera.

9. A device for checking containers, comprising:
   a conveyor for transporting containers;
   one or more light sources;
   two or more cameras; and
   a control unit arranged on the light sources and the cameras,
   wherein the method as claimed in claim 1 is performed by the device for checking containers.

10. The device as claimed in claim 9, wherein two pairs of six pairs of cameras are disposed on either side of the conveyor, and wherein the orientation of each pair differs such that use can be made of stereovision.

11. The device as claimed in claim 9, provided with two or more light sources which each consist of a plurality of LED elements arranged on either side of the conveyor respectively above and opposite a pair of cameras located opposite the conveyor or thereunder.

12. The device as claimed in claim 9, provided with a polarizer for transmitting or holding back a light polarized in a determined manner.

13. The device as claimed in claim 9, provided with a plurality of LEDs.

14. The device as claimed in claim 9, provided with means for placing each container in oblique position and LED lighting which is disposed on either side of the container adjacent to the bottom of the container.

15. The device as claimed in claim 9, wherein one or more prisms and/or mirrors are arranged between a camera and the container for recording images from different sides of the container.

16. The device as claimed in claim 9, provided with a camera disposed adjacent a transition between a neck and a body of the container.

* * * * *